United States Patent [19]

Young

[11] 4,354,677

[45] Oct. 19, 1982

[54] EXERCISING AND TONING DEVICE

[76] Inventor: Robert J. Young, 230 Spring St., Medford, Mass. 02155

[21] Appl. No.: 132,697

[22] Filed: Mar. 21, 1980

[51] Int. Cl.³ .............................................. A63B 23/00
[52] U.S. Cl. ..................................... 272/144; 297/459
[58] Field of Search ................. 272/93, 144, 134, 145; 128/25 R, 68; 297/1, 3, 452, 458, 459, DIG. 2; 4/450, 237, 239, 240, 242, 584, 589, 590; D24/57

[56] References Cited

U.S. PATENT DOCUMENTS

| | | | |
|---|---|---|---|
| 1,546,536 | 7/1925 | Black | 4/590 |
| 1,686,423 | 10/1928 | Thompson | 272/144 |
| 3,503,649 | 3/1970 | Johnson | 297/459 |
| 3,702,204 | 11/1972 | Tipton | 297/DIG. 2 |
| 3,890,004 | 6/1975 | Rail | 297/458 |
| 4,254,514 | 3/1981 | Sakamoto | 4/239 |

Primary Examiner—Richard J. Johnson
Attorney, Agent, or Firm—Wolf, Greenfield & Sacks

[57] ABSTRACT

The device is preferably constructed in the form of a V-shaped buttocks support that may be used on a table or the like for support in a seated position, or on the floor for support in a supine position. From the vertex of the support each leg thereof is similarly contoured with high and low sections, including a high point at the vertex, to enable use of the device, by direct body contact therewith, in different body positions. In either seated or supine positions, the user can direct his or her body weight to various buttocks muscles with the assistance of leg motion to open and close the legs and thus direct contact with the device to different muscle areas. Thus, muscle contraction exercises can be performed with the legs in a stationary position to provide a toning and firming of the exercised muscles.

6 Claims, 8 Drawing Figures

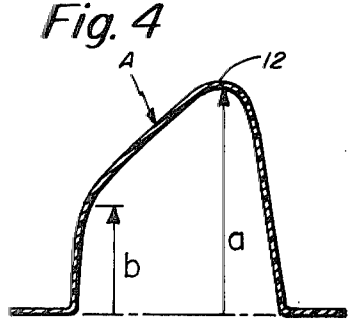
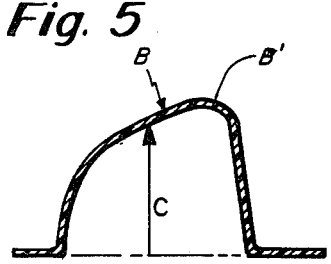
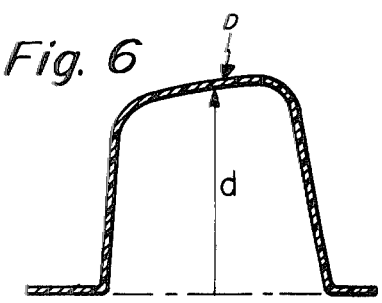
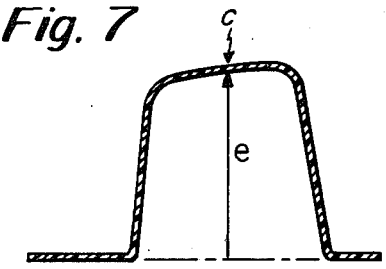
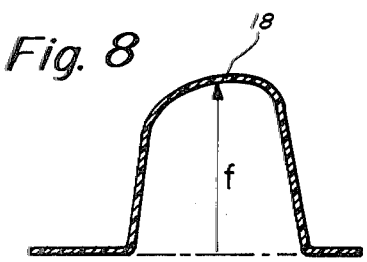

EXERCISING AND TONING DEVICE

BACKGROUND AND SUMMARY OF THE INVENTION

The present invention relates in general to an exercising and toning device, and, more particularly, to a support device for receiving a person's buttocks whereby a series of muscle contraction exercises may be performed, leading to the toning and firming of these exercised muscles.

There have been developed over the years a number of different pieces of apparatus that can be used for the purpose of toning and firming muscles. Also, exercises have been performed without the use of apparatus for toning purposes. However, few, if any, devices have been devised for the purpose of toning and firming the buttocks muscles, which, with the sedentary life style of today, are apt to become flabby and unfirm.

Accordingly, one object of the present invention is to provide a buttocks exercising and toning device having different shaped and arranged contours to enable a person to exercise their buttocks muscles.

Another object of the present invention is to use a buttocks exercising and toning device which may be used with the person either in a seated position or in a supine position.

Another object of the present invention is to provide a buttocks exercising and toning device that is of a relatively simple construction, that is light in weight, and that can be used in a number of different body positions for toning different ones of the buttocks muscles.

To accomplish the foregoing and other objects of this invention, there is provided a device that is constructed in the form of a V-shaped buttocks support preferably of a rigid plastic material that is of a relatively light weight and having the contours that enable a person to exercise the buttocks muscles. The buttocks support is adapted for use either on a table or the like for support therein in a seated position, or on the floor for support therein in a supine position. In a seated position, for example, the user selects one of the many contours of the device, depending upon the particular buttocks muscles that are to be exercised, and with the use of lifting leg movements, the person can develop a series of muscle contraction exercises. By continued use of these exercises, there will be an eventual toning and firming of the buttocks muscles providing that area of the body a more healthy, rounded and more attractive contour. From the vertex of the support each leg thereof is similarly contoured with high and low sections including a high point at the vertex of the buttocks support. In addition, at the ends of the legs opposite the vertex there are provided handles for gripping the support when in use.

BRIEF DESCRIPTION OF THE DRAWINGS

Numerous other objects, features and advantages of the invention should now become apparent upon a reading of the following detailed description taken in conjunction with the accompanying drawings, in which:

FIG. 4 is a cross-sectional view taken at the vertex of the device along line 4—4 of FIG. 2;

FIG. 5 is a cross-sectional view taken along line 5—5 of FIG. 3 through one of the depressed curve sections;

FIG. 6 is a cross-sectional view taken along line 6—6 showing a cross-section through one of the elevated sections of the leg;

FIG. 7 is a cross-sectional view taken along line 7—7 showing a cross-section through a flatter elevated section; and FIG. 8 is a cross-sectional view taken along line 8—8 of FIG. 3 through the handle section of the device.

DETAILED DESCRIPTION

Figure 3:
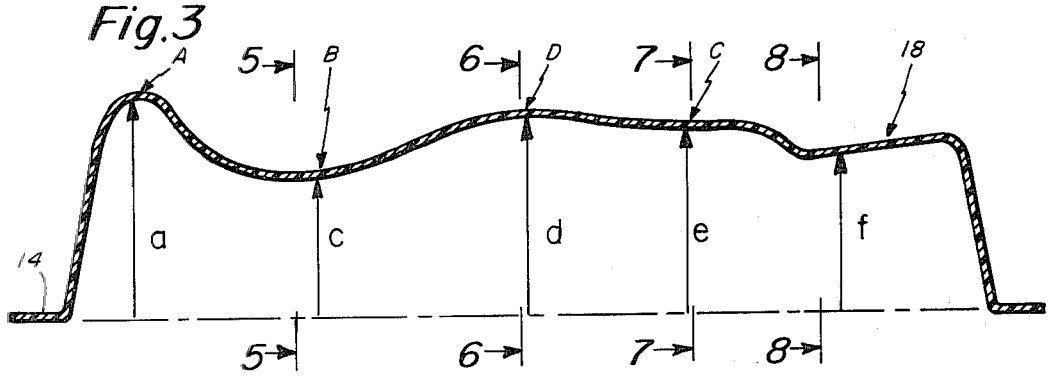
FIG. 3 is a cross-sectional view taken along one leg of the device shown in FIGS. 1 and 2 as depicted along line 3—3 of FIG. 2.

The drawing shows a generally V-shaped buttocks support 10 having legs 10A and 10B. Each of the legs is of substantially identical construction, one forming the mirror image of the other and joining at the vertex 12. The device is adapted to enable a person to exercise their buttocks muscles. It may be used in either a seated position or a supine position and is adapted in either case to lie upon a flat surface. Thus, the device includes a base 14 which in the preferred embodiment extends only about the periphery of the device with the contoured walls forming a hollow chamber open from the bottom. In an alternate arrangement the base 14 could extend under the total width of each leg. From the base 14 extends side walls, such as walls 15 and 16 which are generally vertical walls from the base 14 associated with leg 10A. Of course, there are similarly configured upright walls associated with the other leg 10B. These generally upright walls support a contoured upper wall surface having sections A, B, C and D depicted in FIGS. 1 and 3, and a handle section 18 associated with each leg.

Figure 1:
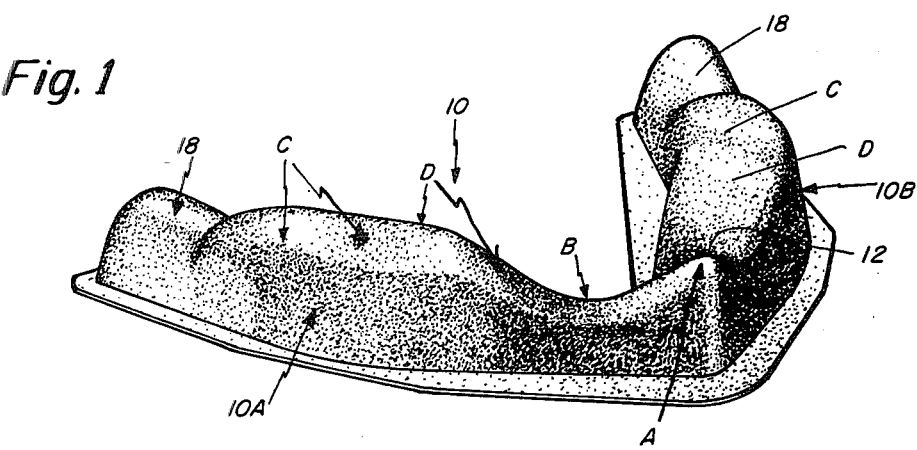
FIG. 1 is a perspective view of a preferred embodiment of the exercising and toning device of this invention.
Figure 2:
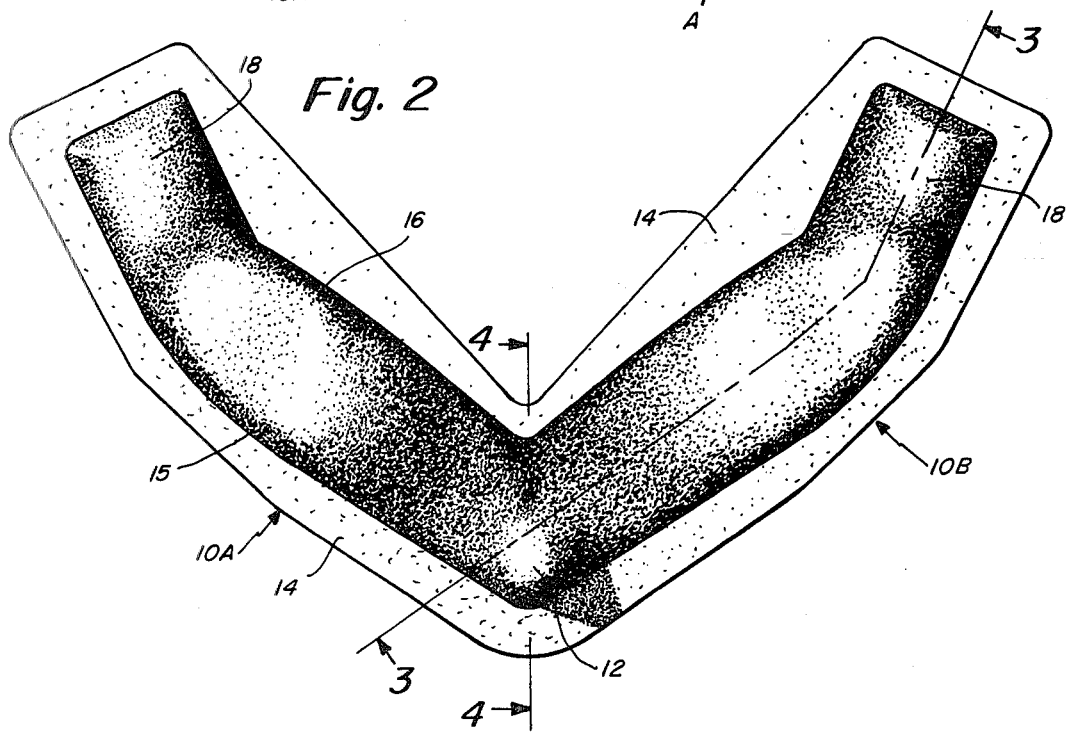
FIG. 2 is a plan view of the device shown in FIG. 1.

One can use the device shown in FIG. 1 by placing different areas or muscles of the buttocks on the different contoured surfaces shown either in a seated position or in a supine position. The body weight may be directed to different ones of the buttocks muscles. Muscle contraction exercises are performed. This procedure eventually leads to the toning and firming of these muscles and gives that area of the body a more healthy, rounded, and attractive contour.

For use in a seated position, the device may be placed at the corner of a table, such as a kitchen table. The vertex 12, or a peaked section A generally faces toward the corner point of the table and the vertex should be at least within a few inches of being directly above the table leg or other supporting structure, so as to provide sufficient support for the weight of the person that is using the device. One can test the support to see that it is sufficient by gradually pressing down on the handles 18 before attempting to use the device. The table or similar supporting structure should be approximately of the same height as the user's lower buttocks, that is when a person is standing, or possibly lower.

FIG. 5 shows a cross-section through the curved section B of the device. This section curves downwardly from the apex 12 and back upwardly to the section D which is actually a transition section between sections B and C. The section B also slopes slightly downwardly at its side walls. The device may be used with the buttocks contacting primarily this section B by using the device on a table and sitting on it so that the bottom line of each buttock cheek is directly on top of an area indicated generally by the reference character B' which is along a forward area of the overall curved section B. The user can then direct all of his or her weight at the lower buttocks muscles. In performing the exercise the legs should be straight and extended outward with feet approximately one foot apart. The person's hands are to the side and possibly slightly rearwardly resting on the handle 18 so as to maintain the proper balance. The person then performs buttock muscle contractions actually causing a lifting of their own body weight. These body contractions may occur with the leg stationary or the contractions may be assisted by slightly raising the legs. The specific areas that are effected can be varied by moving the upper torso from side to side or possibly backwards and forwards with muscle contractions occurring in virtually any position selected. This change in position by moving the upper torso will alter the person's center of gravity and thus put tension on different muscle areas.

Having now described the general positioning for use of the area B, one can now consider the operation with the device for use of the pointed area A. This area is actually not pointed in the traditional sense but is more in the form of a peaked area at the forward side of the apex joining the two legs. Area A is also preferably used in a seated position as described previously with the use of a kitchen table or the like table structure. The user in this position seats him or herself in the device balancing by means of the handles 18 so that the peaked area A is approximately directly below the rectum area. Use in this position requires that the feet preferably be together with the legs extended slightly spaced and just off the floor. This will cause a sufficient spreading of the buttocks cheeks essentially making it more difficult and thus more effective to do the muscle contraction exercises. The peaked area A is preferably disposed at the forward wall 15 centered at the vertex of the device and is, of course, not sharply pointed but rather has a dull rounded top peak.

For use of the sections C and D which are elevated sections, peaked at about the same height as section A, the device is to be used on the floor with the user being in a substantially supine position. With regard to the use of section C the user lies on the device so that the bottom of the buttocks cheeks rest on the top uppermost portion of section C. One side of the buttocks is exercised preferably at a time. The opposite leg is to be bent at the knee to give balance to the rest of the body. In this position muscle contraction exercises are accomplished.

The use of the section D is also accomplished by placing the device on the floor and lying on the device so that the buttocks muscles are on this elevated section D. The buttocks contractions are done substantially the same way as described with regard to section C. One may use the device performing contractions on both cheeks or this does not seem comfortable, then each side may be used one at a time. The buttocks should be moved to direct weight to intended areas before doing each contraction exercise or set of contractions.

The following is a list of typical dimensions that have been employed in the device described in the drawing:
a=3"
b=1½"
c=2"
d=3¾"
e=2½"
f=2¼"

What is claimed is:

1. A portable device for exercising and toning the buttock muscles useable in either a seated or supine position and comprising, a portable base adapted to be positioned on an elevated flat fixed surface, upright means integral with and extending from the base forming two legs extending angularly from a common vertex, each leg having a similarly configured upper wall surface having different elevation sections including a common peak at said vertex, at least one other high elevation section, means integral with each leg for holding the device when used in the seated position, and a lower elevation section of each leg adjacent to and contiguous with the vertex peak, disposed intermediate the vertex peak and said at least one other high elevation section and useable in the seated position for exercising and toning the buttocks muscles, said device adapted for use with the vertex facing forwardly of the user, said upright walls defining a hollow chamber open from the bottom.

2. A device for exercising and toning the buttock muscles useable in either a seated or supine position and comprising, a portable base adapted to be positioned on an elevated flat fixed surface, upright means integral with and extending from the base forming two legs extending angularly from a common vertex, each leg having a similarly configured upper wall surface having different elevation sections including a common peak at said vertex, at least one other high elevation section, means integral with each leg for holding the device when used in the seated position, and a lower elevation section of each leg adjacent to and contiguous with the vertex peak, disposed intermediate the vertex peak said at least one other high elevation section and useable in the seated position for exercising and toning the buttocks muscles, said device adapted for use with the vertex facing forwardly of the user, said legs extending from the vertex at an angle on the order of a right angle and said means integral with each leg comprising a flange that extends outwardly about the periphery of said device.

3. A device as set forth in claim 1 including a slanted section of each leg adjacent said lower elevation section and useable for exercising and toning in a supine position.

4. A device as set forth in claim 3 including a relatively flat high elevation section with the slanted section transitioning between this section and the lower elevation section, said flat high elevation section useable in a supine position.

5. A device as set forth in claim 1 wherein said base includes a peripheral wall extending outwardly from the upright walls.

6. A device for exercising and toning the buttock muscles useable in either a seated or supine position and comprising, a portable base adapted to be positioned on an elevated flat fixed surface, upright means integral with and extending from the base forming two legs extending angularly from a common vertex, each leg having a similarly configured upper wall surface having different elevation sections including a common peak at said vertex, at least one other high elevation section, means integral with each leg for holding the device when used in the seated position, and a lower elevation section of each leg adjacent to and contiguous with the vertex peak, disposed intermediate the vertex peak and said at least one other high elevation section and useable in the seated position for exercising and toning the buttocks muscles, said device adapted for use with the vertex facing forwardly of the user, said legs extending in a V-shape with there being a substantial absence of buttocks engaging surfaces there between.

* * * * *